United States Patent [19]

Rainsford et al.

[11] 4,440,762
[45] Apr. 3, 1984

[54] PROTECTION OF THE GASTRIC MUCOSAL LINING FROM DAMAGE BY ASPIRIN AND RELATED DRUGS

[75] Inventors: Kim D. Rainsford, Kingston Beach; Michael W. Whitehouse, Aranda, both of Australia

[73] Assignee: The Australian National University, Canberra, Australia

[21] Appl. No.: 957,575

[22] Filed: Nov. 3, 1978

[30] Foreign Application Priority Data

Nov. 9, 1977 [AU] Australia ................................... 2352

[51] Int. Cl.$^3$ ............................................. A61U 31/60
[52] U.S. Cl. ..................................................... 424/230
[58] Field of Search ................................ 424/230, 234

[56] References Cited

PUBLICATIONS

Sorokina et al. (Sorokina), Chem. Abstr. 80:5233g(1974).
Moustafa et al. (Moustafa), Chem. Abstr. 85 112717a(1976).
Javaid et al. (Javaid), Chem. Abstr. 77:130533b(1972).
Jue et al., Journal of the Pharm. Ass. pp. 470, 471 & 474 9/63.
Merck Index 7th Ed. (1960) 949–950.
Chem. Abst. (A) 85-140574v(1976).
Chem. Abst. (B) 81-88713r(1974).
Chem. Abst. (C) 68-58407h(1968).
Chem. Abst. (D) 70-50481y(1969).

*Primary Examiner*—Stanley J. Friedman
*Attorney, Agent, or Firm*—Cushman, Darby & Cushman

[57] ABSTRACT

A formulation which allows administration of aspirin and like drugs and avoids gastrointestinal damage to a significant extent is described. A preferred formulation particularly useful for protecting the gastric mucosal lining of arthritic sufferers on a prolonged aspirin medication program comprises aspirin, glucose and sodium acetate or sodium citrate. A like composition containing dibromoaspirin in lieu of aspirin is helpful in reducing gastrointestinal damage to persons suffering from sickle cell disease and who regularly take dibromoaspirin.

3 Claims, No Drawings

PROTECTION OF THE GASTRIC MUCOSAL LINING FROM DAMAGE BY ASPIRIN AND RELATED DRUGS

FIELD OF THE INVENTION

This invention relates to protection of gastric mucosal lining from damage by aspirin and related drugs and to aspirin and like drug formulations which are safer, in the sense of being less gastrotoxic.

DESCRIPTION OF THE PRIOR ART

Gastrointestinal damage (ulceration and haemorrhage) is a serious side effect associated with many analgesics and indeed with many such drugs which are readily available without medical prescription in across the counter transactions: Aspirin itself, dispersed in water (it is not every soluble) causes local injury to gastric mucosa in experimental animals—rats, pigs and monkeys as well as in man. Salts of aspirin, e.g. with ca++, are more soluble but still cause gastric irritations and/or ulcerations. These undesirable effects of both soluble and insoluble aspirin, and like drugs, are accentuated by fasting and by stress: conditions that often pertain when the drug is consumed e.g. in the middle of the night to relieve pain and in the early morning to alleviate the stiffness of arthritis. Although bicarbonate has been widely promoted commercially as preventing gastrotoxicity, our investigations showed this to be not so in stressed animals.

Recent proposals to use aspirin (or its 3,5 dibromo derivative) to prevent haemoglobin stacking in erythrocytes in 'sickle cell disease' and to use aspirin as a prophylactic drug to prevent thrombotic (ischaemic heart) disorders indicate that aspirin will probably remain an essential drug in the therapeutic armoury. Removing the acetyl group of aspirin abolishes both its anti-sickling and its anti-thrombotic effects. However, retention of the acetyl group ensures optimal gastrotoxicity. Therefore further widespread prophylactic use of aspirin may well be determined by any strategy to raise its efficacy:gastrotoxicity ratio.

SUMMARY OF THE INVENTION

A prime project of this invention is to provide a formulation which whilst reducing gastrointestinal damage still retains pharmaceutical potency.

Broadly this invention concerns an analgesic formulation which substantially avoids the undesirable effects adverted to previously and which formulation comprises an aspirin or like analgesic together with a gastroprotectant and a solubilising agent. More than one aspirin like compound, gastroprotectant and solubilising agent may be included in the formulation if desired. Further pharmaceutically acceptable excipients may be added if desired. The formulation may be prepared in solid or liquid (including dispersed) form. A gastroprotectant is intended to relate to an agent which given orally together with aspirin or the like to fasted animals e.g. rats significantly reduces the number and/or the severity of the mucosal lesions or ulcers occuring in the stomach wall that are observed with the same dosage of aspirin or the like alone.

DETAILED DESCRIPTION OF THE INVENTION

The preferred analgesic is aspirin i.e. acetylsalicylic acid but similar compounds and salts i.e. salicylates are intended to be included in the formulation of this invention. The preferred solubilising agents are sodium acetate and sodium citrate but other alkali or alkaline earth metal and ammonium salts of carboxylic acids and phosphoric acid are effective. The preferred gastroprotectant is D-glucose but other metabolizable carbohydrates especially hexoses are effective.

Advantages of the present invention will become clearer from a consideration of the following examples.

EXAMPLE 1

A test formulation (hereinafter called AN-SPIRIN AG) comprising 1 part of aspirin, 3 molar eqivalents of sodium acetate and 3 molar equivalents of D-glucose was formulated in liquid form by dissolution in a minimal amount of water. Surprisingly the lesion index observed in the stomach of rats orally administered with AN-SPIRIN AG was only 7 compared with a lesion index of 36 observed in rats treated with a like amount of aspirin (150 mg/kg) dispersed in water. Lesion index is a measure of gastric mucosal damage (see Rainsford, 1975 Agents and Actions 5, 553). The figures in respect of pig-tail monkeys are even more surprising as a monkey orally administered with aspirin dispersed in water developed 68 lesions whereas a monkey orally administered with a like amount of AN-SPIRIN AG developed only 6 lesions.

EXAMPLE 2

In the foregoing example 1, substitution of sodium citrate for sodium acetate gave analogous results.

EXAMPLE 3

3, 5 Dibromo-o-Acetyl salicyclic acid (dibromoaspirin) at a dose of 150 mg/kg given orally to starved and cold-stressed rats caused gastric haemorrhage within 2 hours, the lesion index was 20.3. Another group of rats, starved and cold-stressed, given orally 150 mg/kg aspirin alone at the same time had a lesion index of 50.8.

Oral administration of 282 mg/kg of dibromoaspirin to a further group of starved and cold-stressed rats together with 3 molar equivalents of D-glucose and 3 molar equivalents of sodium acetate gave a lesion index of only 3.0.

EXAMPLE 4

Substitution of an equivalent amount of di-sodium citrate for the sodium acetate in the foregoing example 3 gave no lesions at all i.e. the lesion index=0.0.

Tests with formulations containing aspirin and sodium acetate (but no D-glucose), and aspirin and D-glucose (but no sodium acetate) showed much less reduction in the number of lesions and their severity compared with the use of aspirin alone. Consequently the remarkable reduction in the number and severity of gastric mucosal lesions occuring when using AN-SPIRIN AG is due to the combination of the three ingredients.

As mentioned previously D-glucose is the preferred gastro-protectant. Tests with fructose and sucrose given orally in combination with sodium citrate or sodium acetate and aspirin showed them to be very effective in reducing gastric mucosal damage. Results obtained with galactose showed it was not as effective as the other sugars tested.

As indicated earlier sodium acetate and sodium citrate are preferred solubilising agents. Particularly effective results have been obtained with formulations of aspirin, glucose and tri-sodium citrate in molar proportions of 1:3:3. Replacement of the tri-sodium citrate by di-sodium citrate gave slightly less effective results.

It is reiterated that the foregoing examples are exemplary only and not intended to be restrictive of the broad scope of the invention.

What we claim is:

1. A pharmaceutical formulation consisting essentially of aspirin, sodium acetate and D-glucose in molar proportions of 1:3:3.

2. A pharamceutical formulation consisting essentially of 3,5 Dibromo-o-Acetyl salicyclic acid, sodium acetate and Di-glucose in molar proportions of 1:3:3.

3. A method of obtaining an analgesic effect while minimizing gastrointestinal damage which might normally accompany administration of an analgesic by itself, which comprises administering to a subject in need of said analgesic effect an effective amount of a composition according to claim 1.

* * * * *